(12) United States Patent
De Bruyn et al.

(10) Patent No.: US 7,358,239 B2
(45) Date of Patent: Apr. 15, 2008

(54) PYRROLIDINYL, PIPERIDINYL OR HOMOPIPERIDINYL SUBSTITUTED (BENZODIOXAN, BENZOFURAN OR BENZOPYRAN) DERIVATIVES

(75) Inventors: Marcel Frans Leopold De Bruyn, Hoogstraten (BE); Kristof Van Emelen, Sint-Niklaas (BE); Piet Tom Bert Paul Wigerinck, Vosselaan (BE); Wim Gaston Verschueren, Anteverpen (BE)

(73) Assignee: Janssen Pharmaceutica, N.V., Beerse (BE)

( * ) Notice: Subject to any disclaimer, the term of this patent is extended or adjusted under 35 U.S.C. 154(b) by 115 days.

(21) Appl. No.: 11/079,606

(22) Filed: Mar. 14, 2005

(65) Prior Publication Data

US 2005/0159406 A1 Jul. 21, 2005

Related U.S. Application Data

(62) Division of application No. 09/980,451, filed as application No. PCT/EP00/04747 on May 23, 2000, now Pat. No. 6,900,222.

(30) Foreign Application Priority Data

Jun. 2, 1999 (EP) .................................. 99201746

(51) Int. Cl.
| | | |
|---|---|---|
| *A61P 1/00* | (2006.01) | |
| *A61K 31/00* | (2006.01) | |
| *A61K 31/55* | (2006.01) | |
| *A61K 31/54* | (2006.01) | |
| *A61K 31/497* | (2006.01) | |
| *A61K 31/4965* | (2006.01) | |
| *A61K 31/517* | (2006.01) | |
| *A61K 31/505* | (2006.01) | |
| *A61K 31/41* | (2006.01) | |
| *A61K 31/415* | (2006.01) | |
| *A61K 31/40* | (2006.01) | |
| *C07D 245/00* | (2006.01) | |
| *C07D 487/00* | (2006.01) | |
| *C07D 243/00* | (2006.01) | |
| *C07D 273/00* | (2006.01) | |
| *C07D 285/00* | (2006.01) | |
| *C07D 239/00* | (2006.01) | |
| *C07D 241/00* | (2006.01) | |
| *C07D 403/00* | (2006.01) | |
| *C07D 417/00* | (2006.01) | |
| *C07D 513/00* | (2006.01) | |
| *C07D 233/00* | (2006.01) | |

(52) U.S. Cl. .................. 514/211.08; 514/218; 514/221; 514/222.5; 514/222.8; 514/254.01; 514/255.05; 514/266.2; 514/269; 514/272; 514/274; 514/362; 514/385; 514/386; 514/389; 514/392; 514/422; 540/460; 540/470; 540/473; 540/492; 540/504; 540/505; 540/506; 540/508; 540/509; 540/514; 540/545; 540/569; 540/571; 540/575; 544/8; 544/11; 544/283; 544/285; 544/286; 544/287; 544/292; 544/298; 544/301; 544/311; 544/316; 544/318; 544/319; 544/320; 544/330; 544/332; 544/335; 544/336; 544/372; 544/408; 548/134; 548/135; 548/311.4; 548/311.7

(58) Field of Classification Search ........... 514/211.08, 514/218, 221, 222.5, 222.8, 254.01, 255.05, 514/266.2, 269, 272, 274, 362, 385, 386, 514/389, 392, 397, 422; 540/460, 470, 473, 540/492, 504, 505, 506, 508, 509, 514, 545, 540/569, 571, 575; 548/134, 135, 311.4, 548/311.7; 544/8, 11, 283, 285, 286, 287, 544/292, 298, 301, 311, 316, 318, 319, 320, 544/330, 332, 335, 336, 372, 408

See application file for complete search history.

(56) References Cited

U.S. PATENT DOCUMENTS

| | | | |
|---|---|---|---|
| 3,910,930 A | 10/1975 | Janssen et al. | 546/199 |
| 3,929,801 A | 12/1975 | Janssen et al. | 546/199 |
| 4,329,348 A | 5/1982 | Huebner | 424/251 |
| 4,470,989 A | 9/1984 | Henning et al. | 424/267 |
| 4,849,335 A | 7/1989 | Hofnung et al. | 435/6 |
| 5,137,901 A | 8/1992 | Junge et al. | 514/323 |
| 5,371,094 A | 12/1994 | Heine et al. | 514/323 |
| 5,492,918 A | 2/1996 | Wild et al. | 514/322 |
| 5,541,199 A | 7/1996 | Mewshaw | 514/314 |
| 5,696,136 A | 12/1997 | Heine et al. | 514/322 |
| 6,133,277 A | 10/2000 | Wigerinck et al. | 514/274 |
| 2004/0019051 A1 | 1/2004 | Van emelen et al. | 514/248 |

FOREIGN PATENT DOCUMENTS

| | | |
|---|---|---|
| DE | 28 52 945 A1 | 6/1980 |
| EP | 0 048 218 A1 | 9/1981 |
| EP | 0004358 B1 | 1/1982 |
| EP | 0 068 261 A1 | 1/1983 |
| EP | 0106749 B1 | 12/1988 |
| GB | 2019838 A | 11/1979 |
| WO | WO 93/17017 A1 | 9/1993 |
| WO | WO 95/05383 A1 | 2/1995 |
| WO | WO 97/28157 A1 | 8/1997 |
| WO | WO 99/29687 A1 | 6/1999 |
| WO | WO 00/75136 A1 | 12/2000 |
| WO | WO 01/98306 A1 | 12/2001 |

OTHER PUBLICATIONS

T. Arakawa et al., New Aspects of Gastric Adaptive Relaxation, Reflex After Food Intake for More Food:Involvement of Capsaicin-senstivie Sensory Nerves and Nitric Oxide, 1997, J. Smooth Muscle Res. 33:81-88.

*Primary Examiner*—Brenda L Coleman
(74) *Attorney, Agent, or Firm*—Woodcock Washburn LLP

(57) ABSTRACT

The present invention concerns compounds of formula (I)

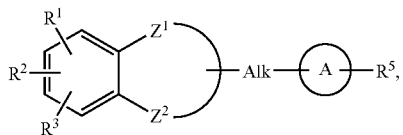

a stereochemically isomeric form thereof, an N-oxide form thereof or a pharmaceutically acceptable acid addition salt thereof, wherein $-Z^1-Z^2-$ is a bivalent radical; $R^1$, $R^2$ and $R^3$ are each independently selected from hydrogen, $C_{1-6}$alkyl, hydroxy, halo and the like; or when $R^1$ and $R^2$ are on adjacent carbon atoms, $R^1$ and $R^2$ taken together may form a bivalent radical of formula; Alk is optionally substituted $C_{1-6}$alkanediyl; the bivalent radical

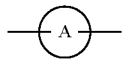

is a substituted piperidinyl, an optionally substituted pyrrolidinyl, homopiperidinyl, piperazinyl or tropyl; $R^5$ is a radical of formula

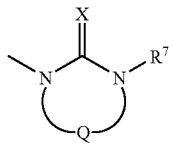 (c-1)

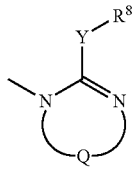 (c-2)

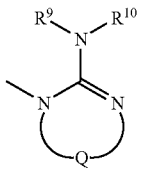 (c-3)

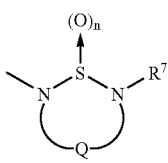 (c-4)

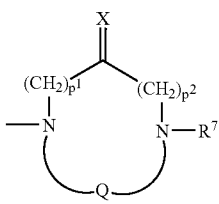 (c-5)

wherein n is 1 or 2; $p^1$ is 0, and $p^2$ is 1 or 2; or $p^1$ is 1 or 2, and $p^2$ is 0; X is oxygen, sulfur or $=NR^9$; Y is oxygen or sulfur; $R^7$ is hydrogen, $C_{1-6}$alkyl, $C_{3-6}$cycloalkyl, phenyl or phenylmethyl; $R^8$ is $C_{1-6}$alkyl, $C_{3-6}$cycloalkyl phenyl or phenylmethyl; $R^9$ is cyano, $C_{1-6}$alkyl, $C_{3-6}$cyclo-alkyl, $C_{1-6}$alkyloxycarbonyl or aminocarbonyl; $R^{10}$ is hydrogen or $C_{1-6}$alkyl; and Q is a bivalent radical. Processes for preparing said products, formulations comprising said products and their use as a medicine are disclosed, in particular for treating conditions which are related to impaired fundic relaxation.

8 Claims, No Drawings

PYRROLIDINYL, PIPERIDINYL OR HOMOPIPERIDINYL SUBSTITUTED (BENZODIOXAN, BENZOFURAN OR BENZOPYRAN) DERIVATIVES

CROSS-REFERENCE TO RELATED APPLICATIONS

This application is a divisional application of U.S. Patent no. 09/980,451, filed Nov. 30, 2001, which is the national stage filing of PCT Application No. PCT/EP00/04747, filed May 23, 2000, which application claims priority from EPO Application No. 99201746.7, filed Jun. 2, 1999, and is incorporated herein by reference.

The present invention is concerned with novel aminomethylchromane compounds having fundic relaxation properties. The invention further relates to methods for preparing such compounds, pharmaceutical compositions comprising said compounds as well as the use as a medicine of said compounds.

Structurally related aminomethylchromane derivatives are disclosed in U.S. Pat. No. 5,541,199 as selective autoreceptor agonists useful as antipsychotic agents. Other structurally related aminomethylchroman derivatives having affinity for cerebral 5-hydroxytryptamine receptors of the 5-HT$_1$ type and therefore suitable for the treatment of disorders of the central nervous system are disclosed in U.S. Pat. No. 5,137,901.

EP-0,546,388, published on 16 Jun. 1993, discloses structurally related aminomethylchroman derivatives having affinity for cerebral 5-hydroxytryptamine receptors of the 5-HT$_1$ type and for dopamine receptors of the D$_2$-type. EP-0,628,310, published on 14 Dec. 1994, encompasses the use of the same aminomethylchroman derivatives for the inhibition of HIV-protease.

DE-2,400,094, published on 18 Jul. 1974, discloses 1-[1-[2-(1,4-benzodioxan-2-yl)-2-hydroxyethyl]-4-piperidyl-2-benzimidazolinones possessing blood pressure lowering activity.

DE-2,852,945, published on 26 Jun. 1980, discloses benzodioaxanylhydroxyethyl-piperidylimidazolidinones having antihypertensive activity.

EP-0,004,358, published on 3 Oct. 1979, discloses N-oxacycloalkylalkylpiperidines useful as antidepressants and psychostimulants.

EP-0,048,218, published on 24 Mar. 1982, discloses N-oxides of N-oxacycloalkylalkylpiperidines having antidepressant activity.

WO-93/17017, published on 2 Sep. 1993, discloses [(benzodioxane, benzofuran or benzopyran)alkylamino]alkyl-substituted guanidine as selective vasoconstrictors useful to treat conditions related to vasodilatation such as, e.g., migraine, cluster headache and headache associated with vascular disorders.

WO-95/053837, published on 23 Feb. 1995, encompasses dihydrobenzopyran-pyrimidine derivatives also having vasoconstrictive activity.

Other structurally related aminomethylchroman derivatives are disclosed in WO-97/28157, published on 7 Aug. 1997, as α$_2$-adrenergic receptor antagonists useful in the treatment of degenerative neurological conditions.

The compounds of the present invention differ from the cited art-known compounds structurally, by the nature of the R$^5$ substituent, and pharmacologically by the fact that, unexpectedly, these compounds have fundic relaxation properties. Furthermore, the compounds of the present invention have additional beneficial pharmacological properties in that they have little or no vasoconstrictor activity.

During the consumption of a meal the fundus, i.e. the proximal part of the stomach, relaxes and provides a "reservoir" function. Patients having an impaired adaptive relaxation of the fundus upon food ingestion have been shown to be hypersensitive to gastric distension and display dyspeptic symptoms. Therefore, it is believed that compounds which are able to normalize an impaired fundic relaxation are useful to relieve patients suffering from said dyspeptic symptoms.

The present invention concerns compounds of formula (I)

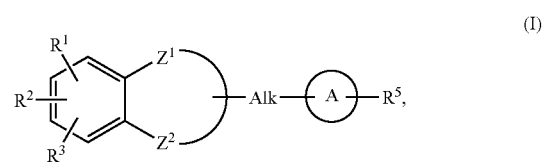

a stereochemically isomeric form thereof, an N-oxide form thereof, a pharmaceutically acceptable acid addition salt thereof, or a quaternary ammonium salt thereof, wherein Alk is C$_{1-4}$alkylcarbonyl, C$_{1-4}$alkylcarbonylC$_{1-4}$alkyl, carbonyl, carbonylC$_{1-4}$alkyl, or C$_{1-6}$alkanediyl optionally substituted with hydroxy, halo, amino, hydroxyC$_{1-4}$alkyl, C$_{1-4}$alkyloxy, C$_{1-4}$alkyloxyC$_{1-4}$alkyl, C$_{1-4}$alkylcarbonyloxy, C$_{1-4}$alkylcarbonyloxyC$_{1-4}$alkyloxycarbonyloxy, or C$_{3-6}$cycloalkylcarbonyloxyC$_{1-4}$alkyloxycarbonyloxy;

-Z$^1$-Z$^2$- is a bivalent radical of formula

 —O—CH(R$^4$)—CH$_2$— (a-1),

 —O—CH(R$^4$)—CH$_2$—O— (a-2),

 —O—CH(R$^4$)—CH$_2$—S— (a-3),

 —O—CH(R$^4$)—CH$_2$—CH$_2$— (a-4),

 —O—CH(R$^4$)—CH$_2$—CH$_2$—CH$_2$— (a-5),

 —O—C(R$^4$)=CH— (a-6),

 —O—C(R$^4$)=CH—CH$_2$— (a-7),

 —O—C(R$^4$)=CH—CH$_2$—CH$_2$— (a-8), or

 —O—CH(R$^4$)—CH=CH— (a-9), wherein optionally one or two hydrogen atoms on the same or a different carbon atom may be replaced by hydroxy;

R$^1$, R$^2$ and R$^3$ are each independently selected from hydrogen, C$_{1-6}$alkyl, C$_{3-6}$alkenyl, C$_{1-6}$alkyloxy, trihalomethyl, trihalomethoxy, halo, hydroxy, cyano, nitro, amino, C$_{1-6}$alkylcarbonylamino, C$_{1-6}$alkyloxycarbonyl, C$_{1-4}$alkylcarbonyloxy, aminocarbonyl, mono- or di(C$_{1-6}$alkyl)aminocarbonyl, aminoC$_{1-6}$alkyl, mono- or di(C$_{1-6}$alkyl)aminoC$_{1-6}$alkyl, C$_{1-4}$alkylcarbonyloxyC$_{1-4}$alkyloxycarbonyloxy, or C$_{3-6}$cycloalkylcarbonyloxyC$_{1-4}$alkyloxycarbonyloxy; or when R$^1$ and R$^2$ are on adjacent carbon atoms, R$^1$ and R$^2$ taken together may form a bivalent radical of formula

| | |
|---|---|
| —CH₂—CH₂—CH₂— | (b-1), |
| —CH₂—CH₂—CH₂—CH₂— | (b-2), |
| —CH₂—CH₂—CH₂—CH₂—CH₂— | (b-3), |
| —CH=CH—CH=CH— | (b-4), |
| —O—CH₂—O— | (b-5), |
| —O—CH₂—CH₂— | (b-6), |
| —O—CH₂—CH₂—O— | (b-7), |
| —O—CH₂—CH₂—CH₂— | (b-8), |
| —O—CH₂—CH₂—CH₂—CH₂— | (b-9), | wherein optionally one or two hydrogen atoms on the same or a different carbon atom may be replaced by hydroxy, $C_{1-4}$alkyl or $CH_2OH$;

$R^4$ is hydrogen, $C_{1-6}$alkyl, phenylmethyl, hydroxy$C_{1-4}$alkyl, $C_{1-4}$alkyloxy$C_{1-4}$alkyl, $C_{1-4}$alkyloxycarbonyl, $C_{1-4}$alkylcarbonyloxy$C_{1-4}$alkyloxycarbonyl, $C_{3-6}$cycloalkylcarbonyloxy$C_{1-4}$alkyloxycarbonyloxy, or a direct bond when the bivalent radical -$Z^1$-$Z^2$- is of formula (a-6), (a-7) or (a-8);

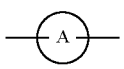

is a bivalent radical of formula

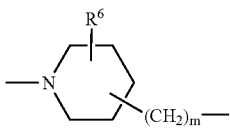 (c-1)

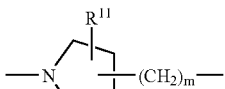 (c-2)

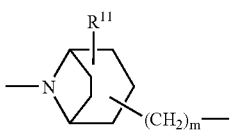 (c-3)

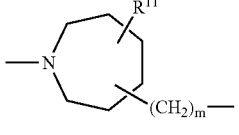 (c-4)

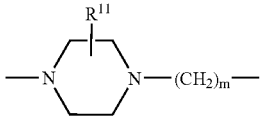 (c-5)

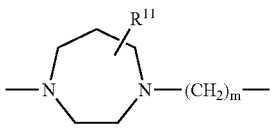 (c-6)

wherein m is 0 or 1;

$R^6$ is $C_{1-4}$alkyl, halo, hydroxy, hydroxy$C_{1-4}$alkyl, $C_{1-4}$alkyloxy, amino$C_{1-4}$alkyl, $C_{1-4}$alkyloxycarbonyl, $C_{1-4}$alkylcarbonyloxy$C_{1-4}$alkyloxycarbonyl, or $C_{3-6}$cycloalkylcarbonyloxy$C_{1-4}$alkyloxycarbonyloxy;

$R^{11}$ is hydrogen, $C_{1-4}$alkyl, halo, hydroxy, hydroxy$C_{1-4}$alkyl, $C_{1-4}$alkyloxy, amino$C_{1-4}$alkyl, $C_{1-4}$alkyloxycarbonyl, $C_{1-4}$alkylcarbonyloxy$C_{1-4}$alkyloxycarbonyl, or $C_{3-6}$cycloalkylcarbonyloxy$C_{1-4}$alkyloxycarbonyloxy;

$R^5$ is a radical of formula

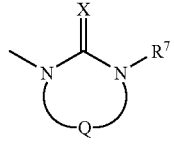 (d-1)

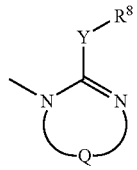 (d-2)

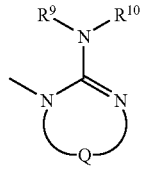 (d-3)

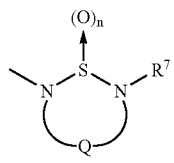 (d-4)

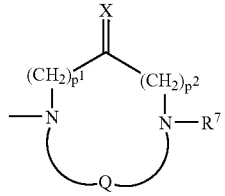 (d-5)

wherein n is 1 or 2;
$p^1$ is 0, and $p^2$ is 1 or 2; or $p^1$ is 1 or 2, and $p^2$ is 0;
X is oxygen, sulfur, $NR^9$ or $CHNO_2$;
Y is oxygen or sulfur;
$R^7$ is hydrogen, $C_{1-6}$alkyl, $C_{3-6}$cycloalkyl, phenyl or phenylmethyl;
$R^8$ is $C_{1-6}$alkyl, $C_{3-6}$cycloalkyl, phenyl or phenylmethyl;
$R^9$ is cyano, $C_{1-6}$alkyl, $C_{3-6}$cycloalkyl, $C_{1-6}$alkyloxycarbonyl or aminocarbonyl;
$R^{10}$ is hydrogen or $C_{1-6}$alkyl;
or $R^9$ and $R^{10}$ taken together with the nitrogen atom to which they are attached may form a pyrrolidinyl, piperidinyl, homopiperidinyl, piperazinyl, or morpholinyl group, optionally substituted with $C_{1-4}$alkyl or $C_{1-4}$alkyloxy; and
Q is a bivalent radical of formula

| | | | |
|---|---|---|---|
| —CH₂—CH₂— | (e-1), | —CO—CH₂— | (e-6), |
| —CH₂—CH₂—CH₂— | (e-2), | —(CH₂)₂—CO— | (e-7), |
| —CH₂—CH₂—CH₂—CH₂— | (e-3), | —CO—(CH₂)₂— | (e-8), |

| -continued | | | |
|---|---|---|---|
| —CH=CH— | (e-4), | —CO—CH$_2$—CO— | (e-9), |
| —CH$_2$—CO— | (e-5), | —CH$_2$—CO—CH$_2$— | (e-10), | wherein optionally one or two hydrogen atoms on the same or a different carbon atom may be replaced by C$_{1-4}$alkyl, hydroxy or phenyl, or Q is a bivalent radical of formula

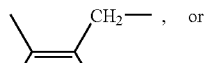     (e-11)

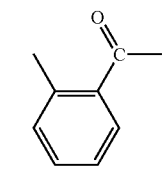     (e-12)

As used in the foregoing definitions halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; C$_{1-6}$alkyl is meant to include C$_{1-4}$alkyl and the higher homologues thereof having 5 or 6 carbon atoms, such as, for example, 2-methyl-butyl, pentyl, hexyl and the like; C$_{3-6}$cycloalkyl is generic to cyclopropyl, cyclobutyl, cyclopentyl and cyclohexyl; C$_{3-6}$alkenyl defines straight and branched chain unsaturated hydrocarbon radicals having from 3 to 6 carbon atoms, such as propenyl, butenyl, pentenyl or hexenyl; C$_{1-2}$alkanediyl defines methylene or 1,2-ethanediyl; C$_{1-5}$alkanediyl defines bivalent straight or branched chain hydrocarbon radicals containing from 1 to 5 carbon atoms such as, for example, methylene, 1,2-ethanediyl, 1,3-propanediyl, 1,4-butanediyl, 1,5-pentanediyl, and the branched isomers thereof; C$_{1-6}$alkanediyl includes C$_{1-5}$alkanediyl and the higher homologues thereof having 6 carbon atoms such as, for example, 1,6-hexanediyl and the like. The term "CO" refers to a carbonyl group.

In compounds of formula (I) wherein the bivalent radical -Z$^1$-Z$^2$- is of formula (a-6), (a-7) or (a-8) the substituent R$^4$ is a direct bond to the

moiety.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention. The tropane moiety (b-3) can have either an endo- or an exo-configuration.

Some examples of the R$^5$ moiety are:

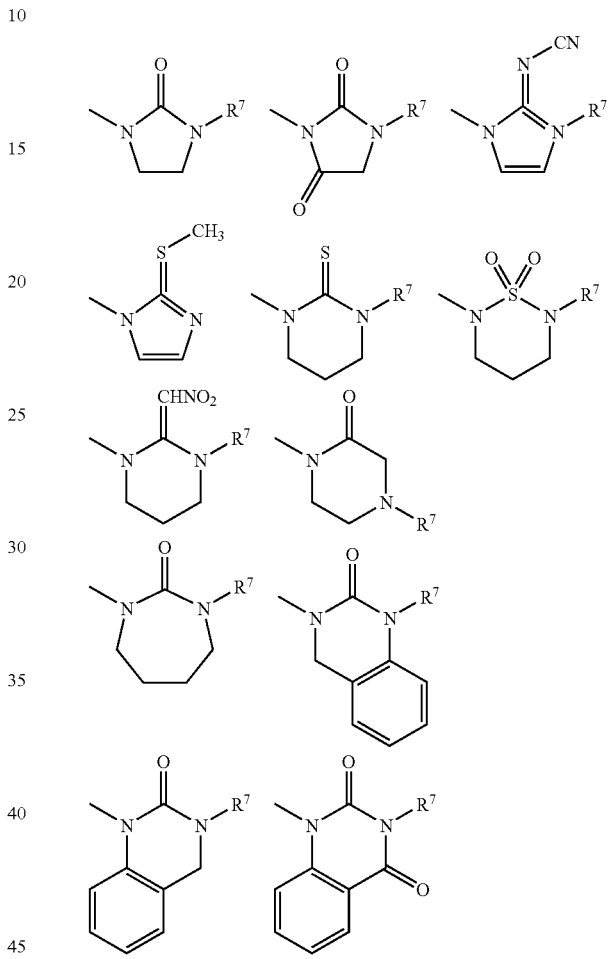

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

Quaternary ammonium salts of compounds of formula (I) as used herein defines which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary ammonium salt has a positively charged nitrogen. Pharmaceutically acceptable counterions include chloro, bromo, iodo, trifluoroacetate and acetate. The counterion of choice can be made using ion exchange resin columns.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of formula (I) wherein the nitrogen atom in the bivalent radical of formula

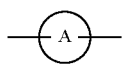

is oxidized to the N-oxide.

Interesting compounds are those compounds of formula (I) wherein one or more of the following restrictions apply:
  a) the bivalent radical $-Z^1-Z^2-$ is of formula (a-1), or (a-6); or
  b) the bivalent radical $-Z^1-Z^2-$ is of formula (a-2), (a-3), (a-4), or (a-9); in particular the bivalent radical $-Z^1-Z^2-$ is of formula (a-3) or (a-4); or
  c) the bivalent radical $-Z^1-Z^2-$ is of formula (a-4);
  d) $R^1$, $R^2$ and $R^3$ are each independently selected from hydrogen, $C_{1-6}$alkyl, hydroxy or halo;
  e) $R^4$ is hydrogen;
  f) Alk is $C_{1-2}$alkanediyl, in particular Alk is $-CH_2-$; or Alk is $C_{1-2}$alkanediyl substituted with hydroxy;
  g) the bivalent radical

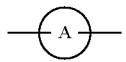

is of formula (c-1) wherein $R^6$ is hydroxy, methoxy, or hydroxymethyl, and m=0, or of formula (c-2) and m=0.

Particular compounds are those compounds of formula (I) wherein $R^5$ is a radical of formula (d-1) wherein X is oxygen, and Q is a radical of formula (e-1) or (e-2).

Preferred compounds are those compounds of formula (I) wherein $R^4$ is hydrogen; $-Z^1-Z^2-$ is of formula $-CH_2-CH_2-$ (a-4), Alk is $-CH_2-$; the bivalent radical

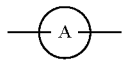

is of formula (c-1) wherein $R^{11}$ is hydroxy or methoxy and m=0; and $R^5$ is a radical of formula (d-1) wherein X is oxygen, $R^7$ is hydrogen, and Q is (e-2).

Other preferred compounds are those compounds of formula: (I) wherein $R^4$ is hydrogen; $-Z^1-Z^2-$ is of formula $-CH_2-CH_2-$ (a-4), Alk is $-CH_2-$; the bivalent radical

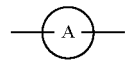

is of formula (c-2) and m=0; and $R^5$ is a radical of formula (d-1) wherein X is oxygen, $R^7$ is hydrogen, and Q is (e-2).

Still other preferred compounds are those compounds of formula (I) wherein $R^4$ is hydrogen; $-Z^1-Z^2-$ is of formula $-CH_2-CH_2-$ (a-4), Alk is $-CH(OH)-CH_2-$; the bivalent radical

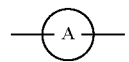

is of formula (c-1), m=0, $R^6$ is hydroxy or hydroxymethyl; and $R^5$ is a radical of formula (d-1) wherein X is oxygen, $R^7$ is hydrogen, and Q is (e-2).

The compounds of the present invention can generally be prepared by alkylating an intermediate of formula (III) with an intermediate of formula (II), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile or tetrahydrofuran, and optionally in the presence of a suitable base such as, for example, sodium carbonate, potassium carbonate, calciumoxide or triethylamine. Stirring may enhance the rate of the reaction. The reaction may conveniently be carried out at a temperature ranging between room temperature and the reflex temperature of the reaction mixture and, if desired, the reaction may be carried out in an autoclave at an increased pressure.

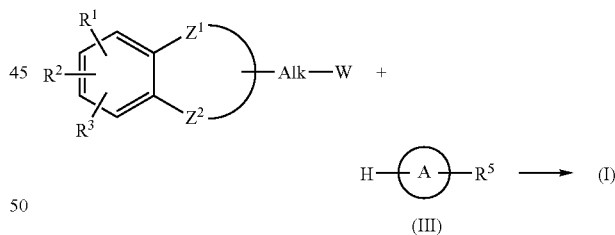

Compounds of formula (I) can also be prepared by reductively alkylating an intermediate of formula (IV), wherein $Alk^1$ represents a direct bond or $C_{1-5}$alkanediyl, following art-known reductive alkylation procedures with an intermediate (III).

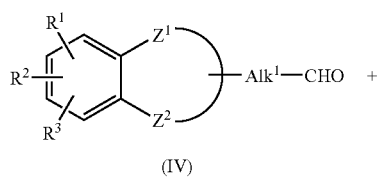

-continued

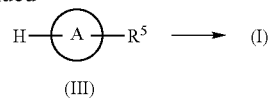

Said reductive alkylation can be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal, rhodium-on-carbon or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

Alternatively, compounds of formula (I) can also be prepared by reacting an acid chloride of formula (V), wherein $Alk^1$ represents $C_{1-5}$alkanediyl or a direct bond, with an intermediate of formula (III) under suitable reaction conditions.

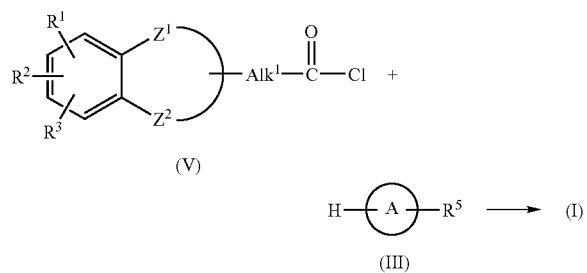

Said reaction can be performed under hydrogenation conditions with hydrogen gas in the presence of a suitable catalyst such as, for example, palladium-on-charcoal, rhodium-on-carbon or platinum-on-charcoal, in a suitable solvent such as, for example, ethyl acetate, and in the presence of magnesiumoxide. In order to prevent the undesired further hydrogenation of certain functional groups in the reactants and the reaction products, it may also be advantageous to add an appropriate catalyst-poison to the reaction mixture, e.g. thiophene or quinoline-sulphur. To enhance the rate of the reaction, the temperature may be elevated in a range between room temperature and the reflux temperature of the reaction mixture and optionally the pressure of the hydrogen gas may be raised.

Compounds of formula (I-a), defined as compounds of formula (I) wherein Alk represents —CH(OH)—CH$_2$—, can be prepared by reacting intermediates of formula (VI) with intermediates of formula (III) in a reaction-inert solvent, such as methanol, and optionally in the presence of an anorganic base, such as sodium carbonate.

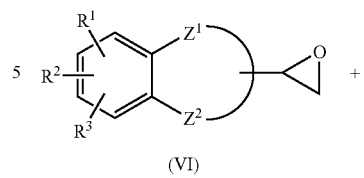

The compounds of formula (I) may further be prepared by converting compounds of formula (I) into each other according to art-known group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid. e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For example, a number of intermediates of formula (II) or (V) may be prepared according to art-known methodologies described in WO-93/17017 and WO-95/053837.

Compounds of formula (I) and some of the intermediates may have one or more stereogenic centers in their structure, present in a R or a S configuration, such as, e.g. the carbon atom bearing the $R^4$ substituent, and the carbon atom linked to the -$Alk^1$-A-$R^5$ moiety.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable salts and stereoisomeric forms thereof possess favourable fundic relaxation properties as evidenced in pharmacological example C-1, the "Gastric tone measured by an electronic barostat in conscious dogs"—test.

Furthermore, the compounds of the present invention have additional beneficial pharmacological properties in that they have little or no vasoconstrictor activity as can be demonstrated in pharmacological example C.2 "Vasoconstrictive activity on basilar artery". Vasconstrictor activity can cause undesirable side-effects such as coronary effects which can induce chest pain.

In view of the capability of the compounds of the present invention to relax the fundus, the subject compounds are useful to treat conditions related to a hampered or impaired relaxation of the fundus such as, e.g. dyspepsia, early satiety, bloating and anorexia.

Dyspepsia is described as a motility disorder. Symptoms can be caused by a delayed gastric emptying or by impaired relaxation of the fundus to food ingestion. Warm-blooded animals, including humans, (generally called herein patients) suffering from dyspeptic symptoms as a result of delayed gastric emptying usually have a normal fundic relaxation and can be relieved of their dyspeptic symptoms by administering a prokinetic agent such as, e.g. cisapride. Patients can have dyspeptic symptoms without having a disturbed gastric emptying. Their dyspeptic symptoms may result from a hypercontracted fundus or hypersensitivity resulting in a diminished compliance and abnormalities in the adaptive fundic relaxation. A hypercontracted fundus results in a diminished compliance of the stomach. The "compliance of the stomach" can be expressed as the ratio of the volume of the stomach over the pressure exerted by the stomach wall. The compliance of the stomach relates to the gastric tone, which is the result of the tonic contraction of muscle fibers of the proximal stomach. This proximal part of the stomach, by exerting a regulated tonic contraction (gastric tone), accomplishes the reservoir function of the stomach.

Patients suffering from early satiety cannot finish a normal meal since they feel saturated before they are able to finish said normal meal. Normally, when a subject starts eating, the stomach will show an adaptive relaxation, i.e. the stomach will relax to accept the food that is ingested. This adaptive relaxation is not possible when the compliance of the stomach is hampered which results in an impaired relaxation of the fundus.

In view of the utility of the compounds of formula (I), it follows that the present invention also provides a method of treating warm-blooded animals, including humans, (generally called herein patients) suffering from impaired relaxation of the fundus to food ingestion. Consequently a method of treatment is provided for relieving patients suffering from conditions, such as, for example, dyspepsia, early satiety, bloating and anorexia.

Hence, the use of a compound of formula (I) as medicine is provided, and in particular the use of a compound of formula (I) for the manufacture of a medicine for treating conditions involving an impaired relaxation of the fundus to food ingestion. Both prophylactic and therapeutic treatment are envisaged.

The symptoms of impaired fundic relaxation may also arise due to the intake of chemical substances, e.g. Selective Seretonine Re-uptake Inhibitors (SSRI's), such as fluoxetine, paroxetine, fluvoxamine, citalopram and sertraline.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxy-propyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense, sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents.

Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository, bases such as cocoa butter or other glycerides.

For intranasal administration the compounds of the invention may be used, for example, as a liquid spray, as a powder or in the form of drops.

The formulations of the present invention may optionally include an anti-flatulent, such as simethicone, alpha-D galactosidase and the like.

In general it is contemplated that a therapeutically effective amount would be from about 0.001 mg/kg to about 2 mg/kg body weight, preferably from about 0.02 mg/kg to about 0.5 mg/kg body weight. A method of treatment may also include administering the active ingredient on a regimen of between two or four intakes per day.

Experimental Part

In the procedures described hereinafter the following abbreviations were used: "ACN" stands for acetonitrile; "THF", which stands for tetrahydrofuran; "DCM" stands for dichloromethane; and "MIK" stands for methyl isobutyl ketone.

For some chemicals the chemical formula was used, e.g. $CH_2Cl_2$ for dichloromethane, $CH_3OH$ for methanol, $NH_3$ for ammonia, HCl for hydrochloric acid, NaOH for sodium hydroxide, and $Na_2CO_3$ sodium carbonate.

In those cases the stereochemically isomeric form which was first isolated is designated as "A" and the second as "B", without further reference to the actual stereochemical configuration.

A. PREPARATION OF THE INTERMEDIATES

Example A.1 a) A mixture of ethyl 3-methoxy-4-oxo-1-piperidinecarboxylate (0.248 mol) and N,N-bis(phenylmethyl)-1,3-propanediamine (0.248 mol) in methanol (600 ml) was hydrogenated at 50° C. with platinum on activated carbon (5%, 5 g) as a catalyst in the presence of thiophene (4%, 5 ml). After uptake of hydrogen (1 equivalent), the catalyst was filtered off and the filtrate was evaporated, yielding 109.8 g of (±)-ethyl 4-[[3-[bis-(phenylmethyl)amino]propyl]amino]-3-methoxy-1-piperidinecarboxylate (interm. 1).

b) A mixture of intermediate (1) (0.25 mol) in methanol (500 ml) was hydrogenated at 50° C. with palladium on activated carbon (5.0 g) as a catalyst. After uptake of hydrogen (2 equivalents), the catalyst was filtered off and the filtrate was evaporated, yielding 66.3 g (102%) of (±)-ethyl 4-[(3-aminopropyl)amino]-3-methoxy-1-piperidine-carboxylate (interm. 2).

c) A mixture of intermediate (2) (0.13 mol) and 1,1'-carbonylbis-1H-imidazole (0.13 mol) in THF (500 ml) was stirred and refluxed overnight. The solvent was evaporated. The residue was crystallized from ACN. The precipitate was filtered off and dried, yielding 20.0 g of (±)-ethyl 3-methoxy-4-(tetrahydro-2-oxo-1(2H)pyrimidinyl)-1-piperidinecarboxylate (interm. 3).

d) A mixture of intermediate (3) (0.0105 mol) in hydrochloric acid (50 ml) and acetic acid (5 ml) was stirred and refluxed overnight. The solvent was evaporated. The residue was dried, yielding 2.05 g (68%) of (±)-tetrahydro-1-(3-methoxy-4-piperidinyl)-2(1H)pyrimidinone dihydrochloride (interm. 4).

Example A.2 a) A mixture of (S)-1-(phenylmethyl)-3-pyrrolidinamine, (0.115 mol) and 2-propenenitrile (0.115 mol) in ethanol (250 ml) was stirred and refluxed for 2 hours. 2-Propenenitrile (1 g) was added and the reaction mixture was stirred and refluxed for another 2 hours. The solvent was evaporated, yielding 27.0 g of (S)-3-[[1-(phenyl-methyl)-3-pyrrolidinyl] amino]propanenitrile (interm. 5).

b) A mixture of intermediate (5) (max. 0.115 mol) in a solution of ammonia in methanol (400 ml) was hydrogenated at a temperature below 20° C. with Raney nickel (3.0 g) as a catalyst. After uptake of hydrogen (2 equivalents), the catalyst was filtered off and the filtrate was evaporated, yielding 28.0 g of (S)—N-[1-(phenylmethyl)-3-pyrrolidinyl]-1,3-propanediamine (interm. 6).

c) A mixture of intermediate (6) (0.12 mol) and 1,1'-carbonylbis-1H-imidazole (0.12 mol) in THF (500 ml) was stirred and refluxed overnight. The solvent was evaporated, yielding 22.5 g of (S)-1-[1-(phenylmethyl)-3-pyrrolidinyl]-2(1H)pyrimidinone (interm. 7).

d) A mixture of intermediate (7) (0.087 mol) in methanol (400 ml) was hydrogenated with palladium on activated carbon (3.0 g) as a catalyst. After uptake of hydrogen (1 equivalent), the catalyst was filtered off and the filtrate was evaporated, yielding 14.3 g of (S)-1-(3-pyrrolidinyl)-2(1H) pyrimidinone (interm. 8).

In an analogous way, (R)-1-(3-pyrrolidinyl)-2(1H)pyrimidinone (interm. 9) was prepared.

Example A.3 a) A. mixture of 4-amino-1-(phenylmethyl)-4-piperidinemethanol (0.0182 mol) and 2-propenenitrile (0.0304 mol) in ethanol (80 ml) was stirred and refluxed over the weekend. 2-Propenenitrile (2 ml) was added. The mixture was stirred and refluxed for 5 hours. 2-Propenenitrile (2 ml) was added again. The mixture was stirred and refluxed overnight. The solvent was evaporated. The residue was purified over silica gel on a glass filter (eluent: $CH_2Cl_2$/($CH_3OH$/NH3) 95/5). The desired fractions were collected and the solvent was evaporated, yielding 3-[[4-(hydroxymethyl)-1(phenylmethyl)-4-piperidinyl]amino]-propanenitrile (interm. 10).

b) A mixture of intermediate (10) (0.0159 mol) in methanol saturated with $NH_3$ (150 ml) was hydrogenated at 14° C. with Raney nickel (½ spoon) as a catalyst. After uptake of hydrogen (2 equivalents), the catalyst was filtered off and the filtrate was evaporated, yielding 3.8 g of 4-[(3-aminopropyl) amino]-1-(phenylmethyl)-4-piperidine-methanol (interm. 11).

c) 1,1'-Carbonylbis-1H-imidazole (0.0149 mol) was added to a mixture of intermediate (11) (0.0137 mol) in THF (40 ml). The mixture was stirred at room temperature overnight. The precipitate was filtered off, crystallized from ACN, filtered off, washed with ACN and DIPE and then dried, yielding 2.05 g of tetrahydro-1-[4-(hydroxy-methyl)-1-(phenylmethyl)-4-piperidinyl]-2(1H)-pyrimidinone (interm. 12, mp. 210° C.).

d) A mixture of intermediate (12) (0.0059 mol) in methanol (100 ml) was hydrogenated with palladium on carbon (1 g) as a catalyst. After uptake of hydrogen (1 equivalent), the catalyst was filtered off, the filtrate was evaporated and crystallized from ACN, yielding 0.6 g of tetrahydro-1-[4-(hydroxymethyl)-4-piperidinyl]-2(1H)-pyrimidinone (interm. 13, mp. 162° C.).

Example A.4 a) A mixture of ethyl 4-(aminomethyl)-4-hydroxy-1-piperidinecarboxylic acid ester (0.0248 mol) and 2-propenenitrile (0.0414 mol) in ethanol (110 ml) was stirred and refluxed for 5 hours. The solvent was evaporated. DCM was added. The solvent was evaporated. Toluene was added. The solvent was evaporated. Again 2-propenenitrile (1.35 ml) and ethanol (110 ml) were added. The mixture was stirred and refluxed overnight. 2-Propenenitrile (1.35 ml) was added again. The mixture was stirred and refluxed for two days. The solvent was evaporated, yielding 5.5 g of ethyl 4-[[(2-cyanoethyl)amino]methyl]-4-hydroxy-1-piperidinecarboxylate (interm. 14).

b) A mixture of intermediate (14) (0.0216 mol) in methanol saturated with $NH_3$ (150 ml) was hydrogenated with Raney nickel (½ spoon) as a catalyst. After uptake of hydrogen (2 equivalents), the catalyst was filtered off, the filtrate was evaporated and purified by column chromatography over silica gel (eluent: $CH_2Cl_2$/($CH_3OH$/$NH_3$) 90/10). The desired fractions were collected and the solvent was evaporated, yielding 3.8 g of ethyl 4-[[(3-aminopropyl) amino]methyl]-4-hydroxy-1-piperidinecarboxylate (interm. 15).

c) 1,1'-Carbonylbis-1H-imidazole (0.016 mol) was added to a mixture of intermediate (15) (0.0147 mol) in THF (50 ml). The mixture was stirred at room temperature overnight. The solvent was evaporated. Water and DIPE were added. The mixture was separated into its layers. The aqueous layer was extracted with DCM. The organic layer was dried, filtered and the solvent was evaporated. The residue was purified by column chromatography over silica gel (eluent: $CH_2Cl_2$/($CH_3OH$/$NH_3$) 97/3). The desired fractions were collected and the solvent was evaporated. The residue was taken up in DIPE. ACN was added. The mixture was warmed up until complete dissolution and then cooled on an ice-bath. The precipitate was filtered off and dried, yielding 1.5 g of ethyl 4-hydroxy-4-[(tetrahydro-2-oxo-1(2H)-pyrimidinyl)methyl]-1-piperidine-carboxylate (interm. 16).

d) A mixture of intermediate (16) (0.1007 mol) and potassium hydroxide (1.0 mol) in 2-propanol (1200 ml) was stirred and refluxed overnight. The solvent was evaporated. Water was added. The solvent was evaporated partially. DCM was added. The organic layer was separated, dried, filtered and the solvent was evaporated. The residue was taken up in ACN. The precipitate was filtered off and dried, yielding tetrahydro-1-[(4-hydroxy-4-piperidinyl)methyl]-2 (1H)-pyrimidinone (interm. 17).

B. PREPARATION OF THE FINAL COMPOUNDS

Example B.1

A mixture of intermediate (4) (0.0072 mol) and (−)-(R)-3,4-dihydro-2H-1-benzopyran-2-carboxaldehyde (0.0092 mol) in methanol (100 ml) was hydrogenated with palladium on activated carbon (2 g) as a catalyst in the presence of thiophene (4%, 1 ml). After uptake of hydrogen (1 equivalent), the catalyst was filtered off and the filtrate was evaporated. The residue was partitioned between water and DCM. The biphasic mixture was alkalized with 50% NaOH, then filtered over dicalite, and the biphasic filtrate was separated into its layers. The organic layer was dried, filtered and the solvent was evaporated, to give a residue. This residue was separated and purified by reversed-phase liquid chromatography over RP-18 (BDS, 8 μm; eluent: (0.5% $NH_4OAc$ in $H_2O$)/$CH_3CN$/$CH_3OH$ 63/7/30). Four pure fraction groups were collected and their solvent was evaporated, yielding 0.4 g [1(R),[A-(3α,4α)]]-1-[1-[(3,4-dihydro-2H-1- benzopyran-2-yl)methyl]-3-methoxy-4-piperidinyl]-2(1H)-pyrimidinone (comp. 1), 0.4 g of [1(R),[B-(3α,4α)]]-1-[1-[(3,4-dihydro-2H-1-benzopyran-2-yl)methyl]-3-methoxy-4-piperidinyl]-2(1H)pyrimidinone (comp. 2), 0.1 g of [1(R),[A-(3α,4α)]]-1-1[(3,4-dihydro-2H-1-benzopyran-2-yl)methyl]-3-hydroxy-4-piperidinyl]-2(1H)pyrimidinone (comp. 3) and 0.1 g of [1(R),[B-(3α,4α)]]-1-[1-[(3,4-dihydro-2H-1-benzopyran-2-yl)methyl]-3-hydroxy-4-piperidinyl]-2(1H)pyrimidinone (comp. 4).

Example B.2

A mixture of intermediate (9) (0.030 mol) and 3,4-dihydro-2H-1-benzopyran-2-carboxaldehyde (0.028 mol) in methanol (100 ml) was hydrogenated at 50° C. with palladium on activated carbon (2.0 g) as a catalyst in the presence of thiophene (4%, 1 ml). After uptake of hydrogen (1 equivalent), the catalyst was filtered off and the filtrate was evaporated. This fraction was pre-purified by column chromatography over silica gel (gradient elution with $CH_2Cl_2$/$CH_3OH$). The desired fractions were collected and the solvent was evaporated. The residue (±5 g) was separated and purified by chiral column chromatography over Chiralcel OD (eluent: hexane/ethanol 80/20). The two pure fraction groups were collected and their solvent was evaporated, yielding 1.75 g of a first fraction and 1.97 g of [3R(B)]-1-[1-[(3,4-dihydro-2H-1-benzopyran-2-yl)methyl]-3-pyrrolidinyl]-2(1H)-pyrimidinone (comp. 6). Said first fraction was further purified by column chromatography over RP BDS Spherical silica gel (Hyperprep C18 BDS 120 Å, 8 μm (Shandon); eluent: [(0.5% $NH_4OAc$ in $H_2O$)/$CH_3CN$ 90/10]/$CH_3OH$/$CH_3CN$ 75/25/0; 0/50/50; 0/0/100; 75/25/0), yielding 0.45 g of [3R(A)]-1-[1-[(3,4-dihydro-2H-1-benzopyran-2-yl)methyl]-3-pyrrolidinyl]-2(1H)pyrimidinone (comp. 5).

Example B.3

A mixture of intermediate (9) (0.031 mol) and 2H-1-benzopyran-3-carboxaldehyde (0.031 mol) in methanol (150 ml) was hydrogenated with palladium on activated carbon (2 g) as a catalyst in the presence of thiophene (4%, 1 ml). After uptake of hydrogen (2 equivalents), the catalyst was filtered off and the filtrate was evaporated. The residue was purified by column chromatography over silica gel (eluent: $CH_2Cl_2$/$CH_3OH$ gradient elution). The desired fractions were collected and the solvent was evaporated. The residue was separated into the enantiomers by chiral column chromatography over Chiralcel OD (eluent: hexane/ethanol 50/50) and further purified by reversed-phase high-performance liquid chromatography over RP-18 (eluent: ((0.5% $NH_4OAc$ in $H_2O$)/$CH_3CN$ 90/10)/$CH_3OH$/$CH_3CN$ (0 min) 68/27/5, (24 min) 38/37/25). The purest fractions were collected and the solvent was evaporated. The residue was dried, yielding 0.90 g of (3R)-1-[1-[(3,4-dihydro-2H-1-benzopyran-3-yl)methyl]-3-pyrrolidinyl]-2(1H)pyrimidinone (comp. 19).

Example B.4

Intermediate (13) (0.0094 mol) was added to a mixture of (R)-3,4-dihydro-2H-1-benzopyran-2-methanol methanesulfonate (ester) (0.0094 mol) and $Na_2CO_3$ (0.0282 mol) in MIK (160 ml). The mixture was stirred and refluxed for a week using a water separator. The solvent was evaporated. Water and DCM were added. The organic layer was separated, washed with water several times, dried, filtered and the solvent was evaporated. The residue was purified by column chromatography over silica gel (eluent: $CH_2Cl_2$/($CH_3OH$/$NH_3$) 90/10). The desired fractions were collected and the solvent was evaporated. The residue was taken up in ACN. The mixture was heated until complete dissolution and then cooled on an ice-bath. The precipitate was filtered off and dried, yielding 0.3 g of compound (20) (mp. 180° C.).

Example B.5

A mixture of [S—(R*,R*)]-3,4-dihydro-2-oxiranyl-2H-1-benzopyran (0.0047 mol), intermediate (17) (0.0047 mol) and $Na_2CO_3$ (0.0042 mol) in ethanol (150 ml) was stirred and refluxed for 2 nights. The solvent was evaporated. Water and DCM were added. The organic layer was separated, dried, filtered and the solvent was evaporated. The residue was taken up in a small amount of ACN. The mixture was heated until complete dissolution and then cooled on an ice bath. The precipitate was filtered off and dried, yielding 0.9 g of compound (30).

Table F-1 and F-2 list the compounds that were prepared according to one of the above Examples. The following abbreviations were used in the tables: .$C_2H_2O_4$ stands for the ethanedioate salt.

TABLE F-1

| Co. No. | Ex. No. | Alk | —(A)— | physical data mp. in ° C. |
|---|---|---|---|---|
| 1 | B.1 | —$CH_2$— | piperidinyl with $OCH_3$, N | [1(R),[A-(3α,4α)]]; mp. 124.3° C. |

TABLE F-1-continued
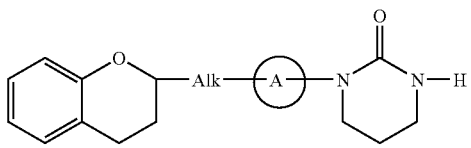
| Co. No. | Ex. No. | Alk | –A– | physical data mp. in ° C. |
|---|---|---|---|---|
| 2 | B.1 | —CH₂— | 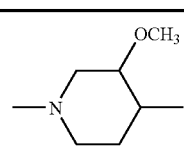 | [1(R),[B-(3α,4α)]]; mp. 158.8° C. |
| 3 | B.1 | —CH₂— | 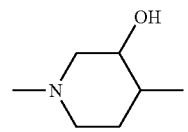 | [1(R),[A-(3α,4α)]]; mp. 172.1° C. |
| 4 | B.1 | —CH₂— | 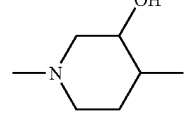 | [1(R),[B-(3α,4α)]]; mp. 153.5° C. |
| 5 | B.2 | —CH₂— |  | [3R(A)] |
| 6 | B.2 | —CH₂— | 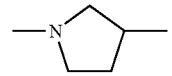 | [3R(B)] |
| 7 | B.1 | —CH₂— | 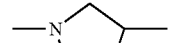 | [3S(A)] |
| 8 | B.1 | —CH₂— | 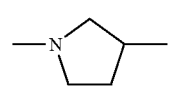 | [3S(B)] |
| 20 | B.4 | —CH₂— |  | (R); mp. 180° C. |
| 21 | B.4 | —CH₂— | 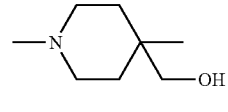 | (S); mp. 200° C.; [α]$_D^{20}$ = +74.82° (c = 26.13 mg/5 ml in methanol) |
| 22 | B.4 | —CH₂— | 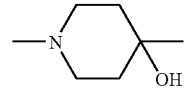 | (S); mp. 178° C. |
| 23 | B.5 | —CH(OH)—CH₂— | 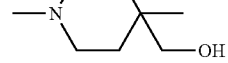 | [R-(R*,R*)] + [S-(R*,R*)] |
| 24 | B.5 | —CH(OH)—CH₂— | 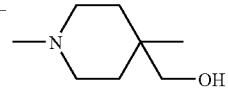 | fraction (B1); mp. 144° C. |

TABLE F-1-continued

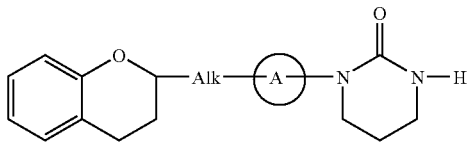

| Co. No. | Ex. No. | Alk | —(A)— | physical data mp. in ° C. |
|---|---|---|---|---|
| 25 | B.5 | —CH(OH)—CH₂— | 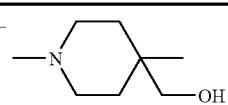 | fraction (B2); mp. 90° C. |
| 26 | B.5 | —CH(OH)—CH₂— | 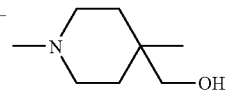 | [R-(R*,S*)] + [S-(R*,S*)] |
| 27 | B.5 | —CH(OH)—CH₂— | 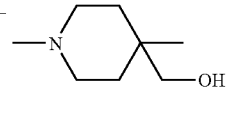 | fraction (A1); mp. 176° C. |
| 28 | B.5 | —CH(OH)—CH₂— |  | fraction (A2); mp. 176° C. |
| 29 | B.5 | —CH(OH)—CH₂— | 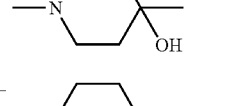 | mp. 182° C.; $[\alpha]_D^{20}$ = −53.68° (c = 25.15 mg/5 ml in methanol) |
| 30 | B.5 | —CH(OH)—CH₂— | 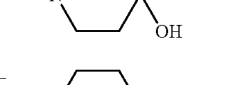 | mp. 182° C.; $[\alpha]_D^{20}$ = +48.91° (c = 25.76 mg/5 ml in methanol) |
| 31 | B.5 | —CH(OH)—CH₂— | 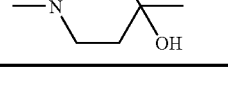 | fraction (A) |

TABLE F-2

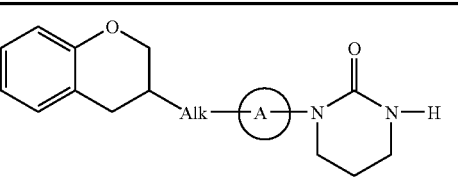

| Co. No. | Ex. No. | Alk | —(A)— | physical data (mp. in ° C.) |
|---|---|---|---|---|
| 9 | B.3 | —CH₂— | 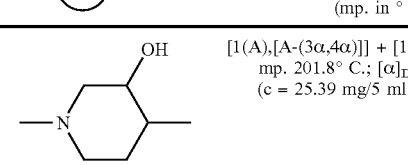 | [1(A),[A-(3α,4α)]] + [1(B),[A-(3α,4α)]]; mp. 201.8° C.; $[\alpha]_D^{20}$ = +57.11° (c = 25.39 mg/5 ml in methanol) |
| 10 | B.3 | —CH₂— | 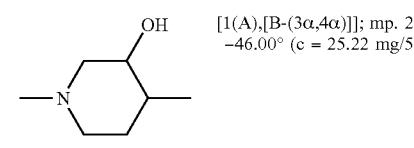 | [1(A),[B-(3α,4α)]]; mp. 200.5° C.; $[\alpha]_D^{20}$ = −46.00° (c = 25.22 mg/5 ml in methanol) |

TABLE F-2-continued

| Co. No. | Ex. No. | Alk | —A— | physical data (mp. in ° C.) |
|---|---|---|---|---|
| 11 | B.3 | —CH$_2$— | 1-methyl-4-methyl-3-hydroxypiperidin-1-yl (OH) | [1(B),[B-(3α,4α)]]; [α]$_D^{20}$ = −85.23° (c = 26.40 mg/5 ml in methanol) |
| 12 | B.3 | —CH$_2$— | 1-methyl-4-methyl-3-methoxypiperidin-1-yl (OCH$_3$) | (CIS) |
| 13 | B.3 | —CH$_2$— | 1-methyl-4-methyl-3-methoxypiperidin-1-yl (OCH$_3$) | [1(A),[A-(3α,4α)]]; [α]$_D^{20}$ = +62.84° (c = 5.57 mg/5 ml in DMF) |
| 14 | B.3 | —CH$_2$— | 1-methyl-4-methyl-3-methoxypiperidin-1-yl (OCH$_3$) | [1(B),[A-(3α,4α)]]; [α]$_D^{20}$ = +103.63° (c = 5.79 mg/5 ml in DMF) |
| 15 | B.3 | —CH$_2$— | 1-methyl-4-methyl-3-methoxypiperidin-1-yl (OCH$_3$) | [1(B),[B-(3α,4α)]]; [α]$_D^{20}$ = −54.67° (c = 7.50 mg/5 ml in DMF) |
| 16 | B.3 | —CH$_2$— | 1-methyl-4-methyl-3-methoxypiperidin-1-yl (OCH$_3$) | [1(A),[B-(3α,4α)]]; mp.197° C.; [α]$_D^{20}$ = −107.35° (c = 6.80 mg/5 ml in DMF) |
| 17 | B.3 | —CH$_2$— | 3-methylpyrrolidin-1-yl | [3A(3S)]; mp. 126.6° C. |
| 18 | B.3 | —CH$_2$— | 3-methylpyrrolidin-1-yl | [3B(3S)]; mp. 113.2° C. |
| 19 | B.3 | —CH$_2$— | 3-methylpyrrolidin-1-yl | (3R) |

PHARMACOLOGICAL EXAMPLES

C.1. Gastric Tone Measured by an Electronic Barostat in Conscious Dogs

Gastric tone cannot be measured by manometric methods. Therefore an electronic barostat was used. This allows the study of the physiological pattern and regulation of gastric tone in conscious dogs and the influence of test-compounds on this tone.

The barostat consists of an air injection system which is connected by a double-lumen 14-French polyvinyl tube to an ultrathin flaccid polyethylene bag (maximal volume: ±700 ml). Variations in gastric tone were measured by recording changes in the volume of air within an intragastric bag, maintained at a constant pressure. The barostat maintains a constant pressure (preselected) within a flaccid air-filled bag introduced into the stomach, changing the volume of air within, the bag by an electronic feedback system.

Thus, the barostat measures gastric motor activity (contraction or relaxation) as changes in intragastric volume (decrease or increase resp.) at a constant intragastric pressure. The barostat consists of a strain gauge linked by an electronic relay to an air injection-aspiration system. Both the strain gauge and the injection system are connected by means of double-lumen polyvinyl tube to an ultrathin polyethylene bag. A dial in the barostat allows selection of the pressure level to be maintained within the intragastric bag.

Female beagle dogs, weighing 7-17 kg, were trained to stand quietly in Pavlov frames. They were implanted with a gastric cannula under general anaesthesia and aseptic precautions. After a median laparotomy, an incision was made through the gastric wall in longitudinal direction between the greater and the lesser curve, 2 cm above the nerves of Latarjet. The cannula was secured to the gastric wall by means of a double purse string suture and brought out via a stub wound at the left quadrant of the hypochondrium. Dogs were allowed a recovery period of two weeks.

At the beginning of the experiment, the cannula was opened in order to remove any gastric juice or food remnants. If necessary, the stomach was cleansed with 40 to 50 ml lukewarm water. The ultrathin bag of the barostat was positioned into the fundus of the stomach through the gastric cannula. In order to ensure easy unfolding of the intragastric bag, during the experiment, a volume of 300-400 ml was injected twice into the bag.

When during a stabilisation period of maximum 90 minutes, the gastric volume is stable during 15 minutes at a constant pressure of 6 mmHg (about 0.81 kPa), the test compound was administered subcutaneously (S.C.), or intraduodenally (I.D.). Test compounds were screened, i.e. changes in gastric volume were measured, usually at 0.63 mg/kg. Other doses and routes were tested if a test compound was shown to be active during the screening procedure. Table C-1 summarizes the mean maximal change in volume on relaxation of the fundus, during the 1 hour observation period after S.C. or I.D. administration of the test compound (0.63 mg/kg);

TABLE C-1

| Co. No. | Route | Maximum change in volume (ml) | Co. No. | Route | Maximum change in volume (ml) |
|---|---|---|---|---|---|
| 2 | S.C. | 9 | 21 | S.C. | 68 |
| 7 | I.D. | 16 | 24 | S.C. | 48 |

TABLE C-1-continued

| Co. No. | Route | Maximum change in volume (ml) | Co. No. | Route | Maximum change in volume (ml) |
|---|---|---|---|---|---|
| 8 | I.D. | 22 | 25 | S.C. | 23 |
| 8 | S.C. | 29 | 27 | S.C. | 46 |
| 20 | I.D. | 178 | 28 | S.C. | 21 |
| 11 | I.D. | 64 | 30 | I.D. | 34 |
| 20 | S.C. | 262 | 31 | I.D. | 26 |

C.2 Vasoconstrictive Activity on Basilar Artery

Segments of basilar arteries taken from pigs (anaesthetised with sodium pentobarbital) were mounted for recording of isometric tension in organ baths. The preparations were bathed in Krebs-Henseleit solution. The solution was kept at 37° C. and gassed with a mixture of 95% $O_2$-5% $CO_2$. The preparations were stretched until a stable basal tension of 2 grams was obtained.

The preparations were made to constrict with serotonin ($3 \times 10^{-7}$ M). The response to the addition of serotonin was measured and subsequently the serotonin was washed away. This procedure was repeated until stable responses were obtained. Subsequently the test compound was administered to the organ bath and the constriction of the preparation was measured. This constrictive response was expressed as a percentage of the response to serotonin as measured previously.

The $ED_{50}$-value (molar concentration) is defined as the concentration at which a test compound causes 50% of the constrictive response obtained with serotonin. Said $ED_{50}$-values are estimated from experiments on three different preparations.

The invention claimed is:

1. A compound of formula (I)

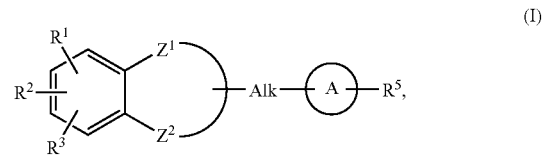

a stereochemically isomeric form thereof, an N-oxide form thereof, a pharmaceutically acceptable acid addition salt thereof, or a quaternary ammonium salt thereof, wherein Alk is $C_{1-4}$alkylcarbonyl, $C_{1-4}$alkylcarbonyl$C_{1-4}$alkyl, carbonyl, carbonyl$C_{1-4}$alkyl, or $C_{1-6}$alkanediyl optionally substituted with hydroxy, halo, amino, hydroxy$C_{1-4}$alkyl, $C_{1-4}$alkyloxy, $C_{1-4}$alkyloxy$C_{1-4}$alkyl, $C_{1-4}$alkylcarbonyloxy, $C_{1-4}$alkylcarbonyloxy$C_{1-4}$alkyloxycarbonyloxy, or $C_{3-6}$cycloalkylcarbonyloxy$C_{1-4}$alkyloxycarbonyloxy;

$-Z^1-Z^2-$ is a bivalent radical of formula

| —O—CH(R⁴)—CH₂— | (a-1), |
| —O—CH(R⁴)—CH₂—O— | (a-2), |
| —O—CH(R⁴)—CH₂—S— | (a-3), |
| —O—CH(R⁴)—CH₂—CH₂— | (a-4), |
| —O—CH(R⁴)—CH₂—CH₂—CH₂— | (a-5), |
| —O—C(R⁴)=CH— | (a-6), |
| —O—C(R⁴)=CH—CH₂— | (a-7), |

-continued

| | |
|---|---|
| —O—C(R⁴)=CH—CH₂—CH₂— | (a-8), or |
| —O—CH(R⁴)—CH=CH— | (a-9), | wherein optionally one or two hydrogen atoms on the same or a different carbon atom may be replaced by hydroxy;

$R^1$, $R^2$ and $R^3$ are each independently selected from hydrogen, $C_{1-6}$alkyl, $C_{3-6}$alkenyl, $C_{1-6}$alkyloxy, trihalomethyl, trihalomethoxy, halo, hydroxy, cyano, nitro, amino, $C_{1-6}$alkylcarbonylamino, $C_{1-6}$alkyloxycarbonyl, $C_{1-4}$alkylcarbonyloxy, aminocarbonyl, mono- or di($C_{1-6}$alkyl)aminocarbonyl, amino$C_{1-6}$alkyl, mono- or di($C_{1-6}$alkyl)amino$C_{1-6}$alkyl, $C_{1-4}$alkylcarbonyloxy-$C_{1-4}$alkyloxycarbonyloxy, or $C_{3-6}$cycloalkylcarbonyloxy$C_{1-4}$alkyloxy-carbonyloxy; or when $R^1$ and $R^2$ are on adjacent carbon atoms, $R^1$ and $R^2$ taken together may form a bivalent radical of formula

| | |
|---|---|
| —CH₂—CH₂—CH₂— | (b-1), |
| —CH₂—CH₂—CH₂—CH₂— | (b-2), |
| —CH₂—CH₂—CH₂—CH₂—CH₂— | (b-3), |
| —CH=CH—CH=CH— | (b-4), |
| —O—CH₂—O— | (b-5), |
| —O—CH₂—CH₂— | (b-6), |
| —O—CH₂—CH₂—O— | (b-7), |
| —O—CH₂—CH₂—CH₂— | (b-8), |
| —O—CH₂—CH₂—CH₂—CH₂— | (b-9), | wherein optionally one or two hydrogen atoms on the same or a different carbon atom may be replaced by hydroxy, $C_{1-4}$alkyl or CH₂OH;

$R^4$ is hydrogen, $C_{1-6}$alkyl, phenylmethyl, hydroxy$C_{1-4}$alkyl, $C_{1-4}$alkyloxy$C_{1-4}$alkyl, $C_{1-4}$alkyloxycarbonyl, $C_{1-4}$alkylcarbonyloxy$C_{1-4}$alkyloxycarbonyl, $C_{3-6}$cycloalkylcarbonyloxy$C_{1-4}$alkyloxycarbonyloxy, or a direct bond when the bivalent radical -$Z^1$-$Z^2$- is of formula (a-6), (a-7) or (a-8);

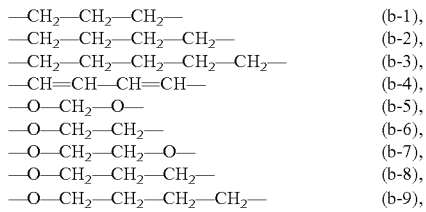

is a bivalent radical of formula

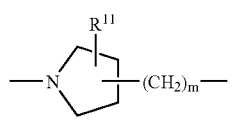
(c-2)

wherein m is 0 or 1;

$R^{11}$ is hydrogen, $C_{1-4}$alkyl, halo, hydroxy, hydroxy$C_{1-4}$alkyl, $C_{1-4}$alkyloxy, amino$C_{1-4}$alkyl, $C_{1-4}$alkyloxycarbonyl, $C_{1-4}$alkylcarbonyloxy$C_{1-4}$alkyloxycarbonyl, or $C_{3-6}$cycloalkylcarbonyloxy$C_{1-4}$alkyloxycarbonyloxy;

$R^5$ is a radical of formula

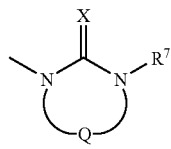
(d-1)

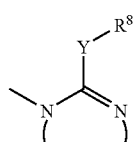
(d-2)

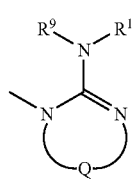
(d-3)

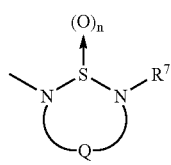
(d-4)

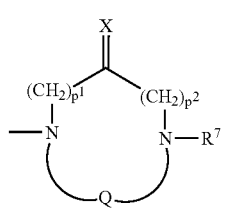
(d-5)

wherein n is 1 or 2;

$p^1$ is 0, and $p^2$ is 1 or 2; $p^1$ is 1 or 2, and $p^2$ is 0;

X is oxygen, sulfur, $NR^9$ or $CHNO_2$;

Y is oxygen or sulfur;

$R^7$ is hydrogen, $C_{1-6}$alkyl, $C_{3-6}$cycloalkyl, phenyl or phenylmethyl;

$R^8$ is $C_{1-6}$alkyl, $C_{3-6}$cycloalkyl, phenyl or phenylmethyl;

$R^9$ is cyano, $C_{1-6}$alkyl, $C_{3-6}$cycloalkyl, $C_{1-6}$alkyloxycarbonyl or aminocarbonyl;

$R^{10}$ is hydrogen or $C_{1-6}$alkyl;

or $R^9$ and $R^{10}$ taken together with the nitrogen atom to which they are attached may form a pyrrolidinyl, piperidinyl, homopiperidinyl, piperazinyl, or morpholinyl group, optionally substituted with $C_{1-4}$alkyl or $C_{1-4}$alkyloxy; and Q is a bivalent radical of formula

| | | | |
|---|---|---|---|
| —CH₂—CH₂— | (e-1), | —CO—CH₂— | (e-6), |
| —CH₂—CH₂—CH₂— | (e-2), | —(CH₂)₂—CO— | (e-7), |
| —CH₂—CH₂—CH₂—CH₂— | (e-3), | —CO—(CH₂)₂— | (e-8), |
| —CH=CH— | (e-4), | —CO—CH₂—CO— | (e-9), |
| —CH₂—CO— | (e-5), | —CH₂—CO—CH₂— | (e-10), | wherein optionally one or two hydrogen atoms on the same or a different carbon atom may be replaced by $C_{1-4}$alkyl, hydroxy or phenyl, or Q is a bivalent radical of formula

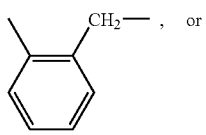 (e-11)

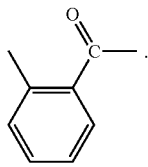 (e-12)

2. A compound as claimed in claim 1 wherein $R^5$ is a radical of formula (d-1) wherein X is oxygen, and Q is a radical of formula (e-1) or (e-2).

3. A compound as claimed in claim 1 wherein $R^4$ is hydrogen; -$Z^1$-$Z^2$- is of formula (a-4), Alk is —$CH_2$—; the bivalent radical

is of formula (c-2) wherein $R^{11}$ is hydroxy or methoxy and m=0; and $R^5$ is a radical of formula (d-1) wherein X is oxygen, $R^7$ is hydrogen, and Q is (e-2).

4. A compound according to claim 1 wherein $R^4$ is hydrogen; -$Z^1$-$Z^2$- is of formula (a-4), Alk is —$CH_2$—; the bivalent radical

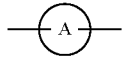

is of formula (c-2) and m=0; and $R^5$ is a radical of formula (d-1) wherein X is oxygen, $R^7$ is hydrogen, and Q is (e-2).

5. A pharmaceutical composition comprising a pharmaceutically acceptable carrier and a therapeutically active amount of a compound as claimed in claim 1.

6. A process for preparing a pharmaceutical composition as claimed in claim 5 comprising combining a therapeutically active amount of said compound with a pharmaceutically acceptable carrier.

7. A process for preparing a compound of formula (I) wherein
   a) an intermediate of formula (II) is alkylated with an intermediate of formula (III) in a reaction-inert solvent and, optionally in the presence of a suitable base,

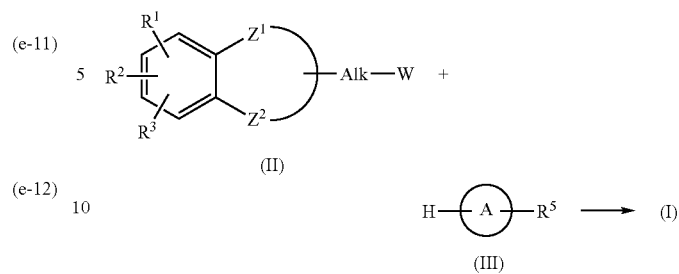

b) an intermediate of formula (IV), wherein $Alk^{1'}$ represents a direct bond or $C_{1-5}$alkanediyl, is reductively alkylated with an intermediate of formula (III);

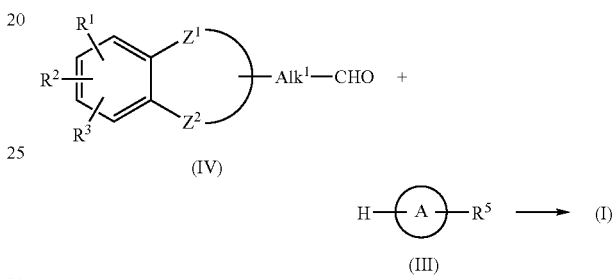

wherein in the above reaction schemes the radicals -$Z^1$-$Z^2$-, $R^1$, $R^2$, $R^3$, $R^5$, Alk and the bivalent radical

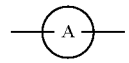

are as defined in claim 1 and W is an appropriate leaving group;

c) or, compounds of formula (I) are converted into each other following art-known transformation reactions; or if desired; a compound of formula (I) is converted into an acid addition salt, or conversely, an acid addition salt of a compound of formula (I) is converted into a free base form with alkali; and, if desired, preparing stereochemically isomeric forms thereof.

8. A method of treating conditions related to a hampered or impaired relaxation of the fundus comprising administering to a subject in need thereof an effective amount of a compound as claimed in claim 1.

* * * * *